United States Patent
Lin et al.

(10) Patent No.: US 10,799,495 B2
(45) Date of Patent: Oct. 13, 2020

(54) AAPTAMINE ALKALOID DERIVATIVES AND SYNTHESIS METHOD AND APPLICATION THEREOF

(71) Applicant: RENJI HOSPITAL, SHANGHAI JIAO TONG UNIVERSITY SCHOOL OF MEDICINE, Shanghai (CN)

(72) Inventors: Houwen Lin, Shanghai (CN); Fan Yang, Shanghai (CN)

(73) Assignee: RENJI HOSPITAL, SHANGHAI JIAO TONG UNIVERSITY SCHOOL OF MEDICINE, Shanghai (CN)

( * ) Notice: Subject to any disclaimer, the term of this patent is extended or adjusted under 35 U.S.C. 154(b) by 0 days.

(21) Appl. No.: 16/477,748

(22) PCT Filed: Jul. 28, 2017

(86) PCT No.: PCT/CN2017/094852
§ 371 (c)(1),
(2) Date: Jul. 12, 2019

(87) PCT Pub. No.: WO2018/129904
PCT Pub. Date: Jul. 19, 2018

(65) Prior Publication Data
US 2019/0350926 A1 Nov. 21, 2019

(30) Foreign Application Priority Data

Jan. 13, 2017 (CN) .......................... 2017 1 0026229

(51) Int. Cl.
*A61K 31/4745* (2006.01)
(52) U.S. Cl.
CPC ................. *A61K 31/4745* (2013.01)
(58) Field of Classification Search
CPC .................................................. A61K 31/4745
See application file for complete search history.

(56) References Cited

U.S. PATENT DOCUMENTS

2005/0187240 A1* 8/2005 Pettit .................... C07D 471/06
514/283

FOREIGN PATENT DOCUMENTS

CN 103936733 A 7/2014
CN 103936734 A 7/2014

OTHER PUBLICATIONS

Nakamura, H., et al.; "Isolation and Structure of Aaptamine a Novel Heteroaromatic Substance Possessing α-Blocking Activity from the Sea Sponge *Aaptos aaptos*"; Tetrahedron Letters, Sep. 24, 1982, vol. 23, No. 52, pp. 5555-5558.
Larghi, E.L., et al.; "Aaptamine and Related Products. Their Isolation, Chemical Syntheses, and Biological Activity"; Feb. 2, 2009, Tetrahedron vol. 65, Report No. 875, pp. 4257-4282.

* cited by examiner

*Primary Examiner* — Timothy R Rozof
(74) *Attorney, Agent, or Firm* — Muncy, Geissler, Olds & Lowe, P.C.

(57) ABSTRACT

A benzodiazepine alkaloid compound and a pharmaceutically acceptable salt thereof, the structure of the compound being shown in general formula (I).

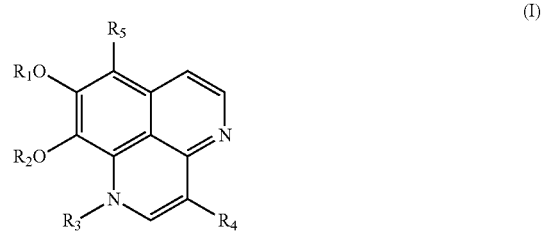

in the formula (I), $R_1$, $R_2$ and $R_3$ independently are hydrogen, $C_{1-4}$ alkyl or $C_{1-4}$ alkanoyl; one from among $R_4$ and $R_5$ is a benzene ring or a substituted benzene ring, while the other is hydrogen, a benzene ring or a substituted benzene ring, wherein a substituent group on the substituted benzene ring is hydroxyl, cyano, amino, halogen, $C_{1-4}$ alkyl, $C_{1-4}$ alkoxy, $C_{1-4}$ alkylamine, $C_{1-4}$ alkanoyl or $C_{1-4}$ alkoxyacyl. A method for synthesizing the compound and a use in the preparation of anti-tumor drugs. The compound shown in formula (I) may be used for preparing anti-tumor, especially anti-lung cancer, drugs as well as anti-fungal drugs.

10 Claims, No Drawings

AAPTAMINE ALKALOID DERIVATIVES AND SYNTHESIS METHOD AND APPLICATION THEREOF

CROSS-REFERENCE TO RELATED APPLICATION

This application claims priority from Chinese Patent Application No. 201710026229.6, filed on Jan. 13, 2017, in State Intellectual Property Office of P.R.China, the contents of which are hereby incorporated by reference in their entirety for all purposes.

BACKGROUND OF THE INVENTION

1. Technical Field

The present invention relates to the technical field of medicine, in particular to Aaptamine alkaloid derivatives (i.e., benzodiazepine alkaloid compounds) and a synthesis method and application thereof in anti-tumor and antifungal fields.

2. Description of Related Art

Alkaloids are a class of nitrogen-containing basic organic compounds found in nature (plants and animals). Most have N-containing complex cyclic structures which have significant biological activities.

Molecules with a benzodiazepine parent nucleus structure are a special class of alkaloids that continue to receive attention due to their unique structural skeleton and biological activities. Aaptamine is the most typical of such alkaloids (Nakamura, H.; Kobayashi, J.; Ohizumi, Y; Hirata, Y. Isolation and structure of aaptamine a novel heteroaromatic substance possessing α-blocking activity from the sea sponge *Aaptosaaptos. Tetrahedron Lett.* 1982, 23, 5555-5558). Aaptamine alkaloids exhibit various biological activities such as antioxidant, enzyme inhibition, antiviral, anti-inflammatory, anti-fouling, anti-depression and anti-tumor activities (Larghi, E L; Bohn, M L; Kaufman, T S, Aaptamine and related products. Their isolation, chemical syntheses, and biological activity. *Tetrahedron* 2009, 65 (22), 4257-4282.), and is considered to be a hot spot for marine innovative drug R&D.

The inventors also conducted related research on Aaptamine alkaloids from Xisha Islands sponge *Aaptos* in the early stage, and disclosed the antitumor activity of the alkaloid compounds. For details, see Chinese Patent CN201410180478.7, entitled "Aaptamine Alkaloid Compound Extracted from Aaptos and Application thereof to Preparation of Antitumor Medicines", with No. of Announcement of Grant being CN103936733B, and the Chinese Patent CN201410181585.1 for invention, entitled "Aaptamine Alkaloid Compound in Sponge from Paracel Islands and Anti-tumor Application of alkaloid Compound", with No. of Announcement of Grant being CN103936734B.

BRIEF SUMMARY OF THE INVENTION

The present invention uses Aaptamine as a parent nucleus for chemical modification research, and is intended to provide a benzodiazepine alkaloid compound having anti-tumor and antifungal activities, and pharmaceutically acceptable salts thereof.

The structure of the compound is as shown in a general formula (I):

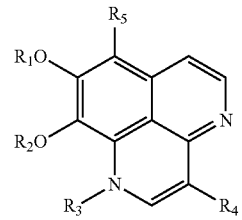

(I)

in the formula (I), $R_1$, $R_2$ and $R_3$ are independently H, $C_{1-4}$ alkyl or $C_{1-4}$ alkanoyl;

one of $R_4$ and $R_5$ is a benzene ring or a substituted benzene ring, the other is H, a benzene ring or a substituted benzene ring (i.e., $R_4$ and $R_5$ are H, benzene rings or substituted benzene rings, but $R_4$ and $R_5$ are not H at the same time), and a substituent on the substituted benzene ring is hydroxyl, cyano, amino, halogen, $C_{1-4}$ alkyl, $C_{1-4}$ alkoxy, $C_{1-4}$ alkylamine, $C_{1-4}$ alkanoyl or $C_{1-4}$ alkoxyacyl.

Preferably, $R_1$ and $R_2$ are methyl and $R_3$ is H.

Preferably, the substituted benzene ring is a monosubstituted or disubstituted benzene ring.

The halogen is preferably $F_1$, $C_1$ or Br; the $C_{1-4}$ alkyl is preferably methyl or isopropyl; and the $C_{1-4}$ alkoxy is preferably methoxy.

Further, the present invention provides partially preferred compounds and pharmaceutically acceptable salts thereof, and the chemical structural formulas of the compounds are specifically as follows:

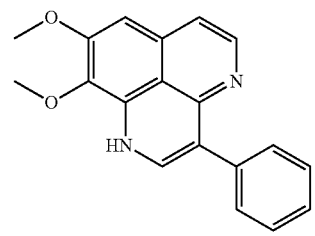

APP-1

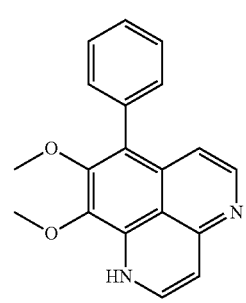

APP-2

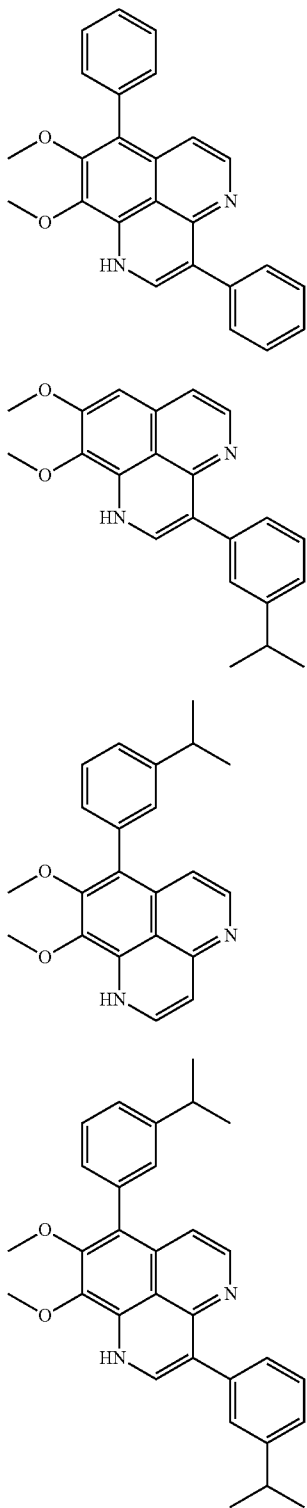

The chemical name of AAP-1 is 8,9-dimethoxy-3-phenyl-1H-benzo[de][1,6]naphthyridine, and its molecular formula is $C_{19}H_{16}N_2O_2$.

The chemical name of AAP-2 is 8,9-dimethoxy-7-phenyl-1H-benzo[de][1,6]naphthyridine, and its molecular formula is $C_{19}H_{16}N_2O_2$.

The chemical name of AAP-3 is 8,9-dimethoxy-3,7-phenyl-1H-benzo[de][1,6]naphthyridine, and its molecular formula is $C_{31}H_{32}N_2O_2$.

The chemical name of AAP-4 is 3-(3-isopropyphenyl)-8,9 dimethoxy-1H-benzo[de][1,6]naphthyridine, and its molecular formula is $C_{22}H_{22}N_2O_2$.

The chemical name of AAP-5 is 7-(3-isopropyphenyl)-8,9 dimethoxy-1H-benzo[de][1,6]naphthyridine, and its molecular formula is $C_{22}H_{22}N_2O_2$.

The chemical name of AAP-6 is 3,7-bis(3-isopropyphenyl)-8,9dimethoxy-1H-benzo[de][1,6] naphthyridine, and its molecular formula is $C_{31}H_{32}N_2O_2$.

The pharmaceutically acceptable salts are salts of an organic acid, salts of an inorganic acid or salts of an alkali.

The inorganic acid is hydrochloric acid, sulfuric acid, phosphoric acid, diphosphoric acid, hydrobromic acid or nitric acid.

The organic acid is acetic acid, maleic acid, fumaric acid, tartaric acid, succinic acid, lactic acid, p-toluenesulfonic acid, salicylic acid or oxalic acid.

The alkali is lithium hydroxide, sodium hydroxide, calcium hydroxide, potassium hydroxide, aqueous ammonia, sodium carbonate or sodium hydrogencarbonate.

Another object of the present invention is to provide a method for synthesizing the benzodiazepine alkaloid compound, comprising the steps of:

(a) carrying out a bromine substitution reaction between an intermediate A and $Br_2$ to obtain a monobromo or dibromo intermediate B; and (b) reacting the intermediate B with phenylboronic acid or substituted phenylboronic acid to obtain a compound of formula (I);

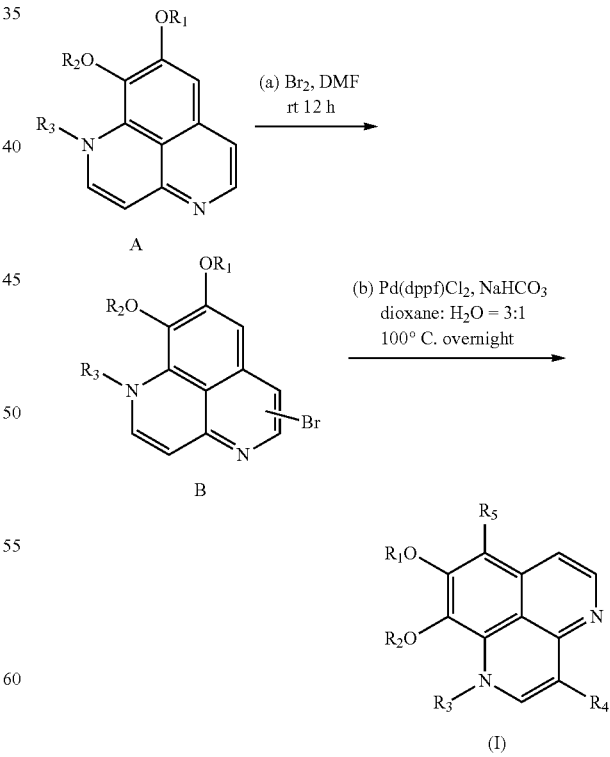

wherein $R_1$, $R_2$ and $R_3$ are independently H, $C_{1-4}$ alkyl or $C_{1-4}$ alkanoyl; one of $R_4$ and $R_5$ is a benzene ring or a substituted benzene ring, the other is H, a benzene ring or a substituted benzene ring, and a substituent on the substituted benzene ring of phenylboronic acid is hydroxyl, cyano, amino, halogen, $C_{1-4}$ alkyl, $C_{1-4}$ alkoxy, $C_{1-4}$ alkylamine, $C_{1-4}$ alkanoyl or $C_{1-4}$ alkoxyacyl.

For the synthesis of the intermediate A, reference is made to *Tetrahedron* 2009, 65 (22), 4257-4282.

A third object of the present invention is to provide application of the benzodiazepine alkaloid compound and pharmaceutically acceptable salts thereof in preparation of an anti-tumor drug, particularly in preparation of anti-lung cancer and antibacterial drugs.

The beneficial effects of the present invention are as follows: The compound represented by the formula (I) of the present invention has a strong inhibitory activity against human lung cancer stem cell PC9-Nanog and human lung cancer stem cell PC9-Oct4, and has obvious anti-lung cancer activity and thus can be used to prepare anti-tumor, especially anti-lung cancer drugs. The compound of the formula (I) of the present invention has a significant inhibitory effect on three tested strains, i.e., *Candida albicans, Trichophyton mentagrophytes* and *Trichophyton rubrum*; especially for *Trichophyton rubrum*, the MIC of the compound is 3.125 μg/mL, which is superior to the positive control drugs ketoconazole (MIC=8 μg/mL) and Aaptamine (MIC>30 μg/mL). Further, the compound represented by the formula (I) may be prepared from the benzodiazepine parent nucleus intermediate A through bromination and catalytic coupling, and the synthesis method is simple.

The present invention provides new lead compounds for the research and development of new anti-tumor and antibacterial drugs.

DETAILED DESCRIPTION OF THE INVENTION

The present invention will now be further described in conjunction with specific embodiments. It should be understood that the following embodiments are merely illustrative of the invention and are not intended to limit the scope of the invention.

Embodiment 1 Synthesis of Compounds APP-1-APP-6

1) Synthesis of Intermediate 3

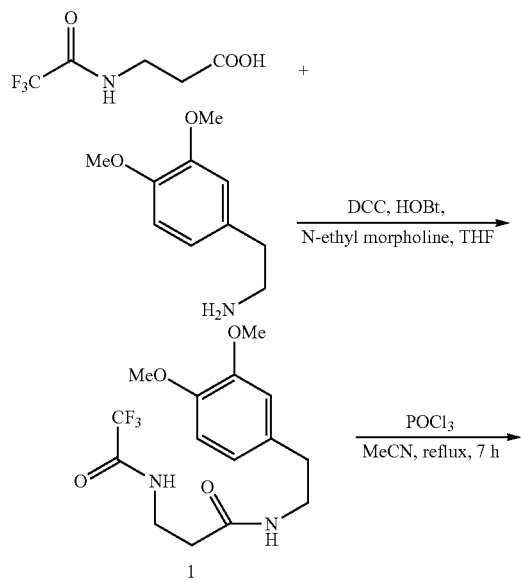

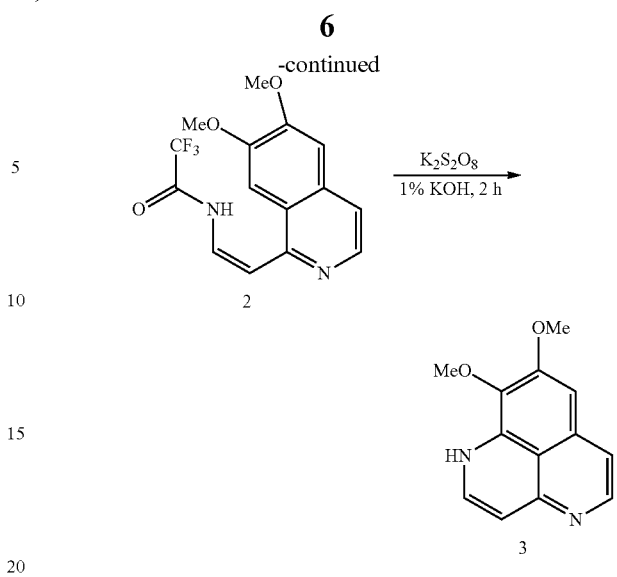

For the synthesis of intermediates 1-3, see *Tetrahedron* 2009, 65 (22), 4257-4282.

3,4-Dimethylphenylethylamine (purchased from Sigma-Aldrich, 2 g, 11 mmol), N-(trifluoroacetyl)-β-alanine (purchased from Sigma-Aldrich, 2 g, 10.8 mmol)), HOBt (1 g, 8.5 mmol) and N-ethylmorpholine (1.5 mL, 10.8 mmol) are mixed and dissolved in THF (16.5 mL), and the mixed solution is added dropwise to a THF solution of DCC (2.5 g, 12 mmol) and reacts for 6 hours at room temperature; the resulting solution is cooled to 0° C. and then filtered; the filtrate is concentrated, and the obtained solid is dissolved in 30 mL of EtOAc, and then rinsed with saturated NaHCO₃ (40 mL), citric acid (20 mL), saturated NaHCO₃ (10 mL), brine and sufficient dry MgSO₄ in sequence and concentrated to obtain an intermediate 1 (2.2 g).

The intermediate 1 is dissolved in CH₃CN (14 mL); POCl₃ (9.5 mL, 0.1 mmol) is added dropwise to the solution, stirred and mixed to carry out reflux reaction at room temperature for 7 hours, and then cooled; the resulting solution is neutralized with saturated NaHCO₃ and then extracted with EtOAc (3×30 mL); the combined EtOAc layer is rinsed with saturated NaHCO₃ (30 mL), concentrated brine (20 mL) and sufficient dry MgSO₄; and the water layer is evaporated to dryness to obtain an intermediate 2 (1.5 g).

The intermediate 2 is dissolved in a 1% KOH solution under a nitrogen atmosphere, and then K₂S₂O₈ (3 eq.) is added to the solution to react at room temperature for 2 hours to obtain an intermediate 3.

2) Synthesis of Intermediate XG03

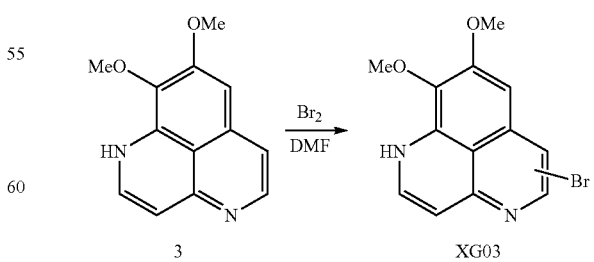

The Intermediate 3 (265 mg) is dissolved in 2 mL of CDCl₃; a solution of Br₂ (160 mg) dissolved in 2 mL of CDCl₃ is added to the mixed solution and is stirred to react for 12 hours at room temperature in a nitrogen atmosphere; and LC-MS shows reaction products as follows: 4% of starting material, 36% of monobromide and 58% of a mixture of monobromo and dibromo in different positions. The reaction solution is concentrated to obtain a mixture of two monobromos and one dibromide, i.e., XG03 (425 mg), which is directly used for the next reaction.

3) Synthesis of AAP-1, AAP-2 and AAP-3

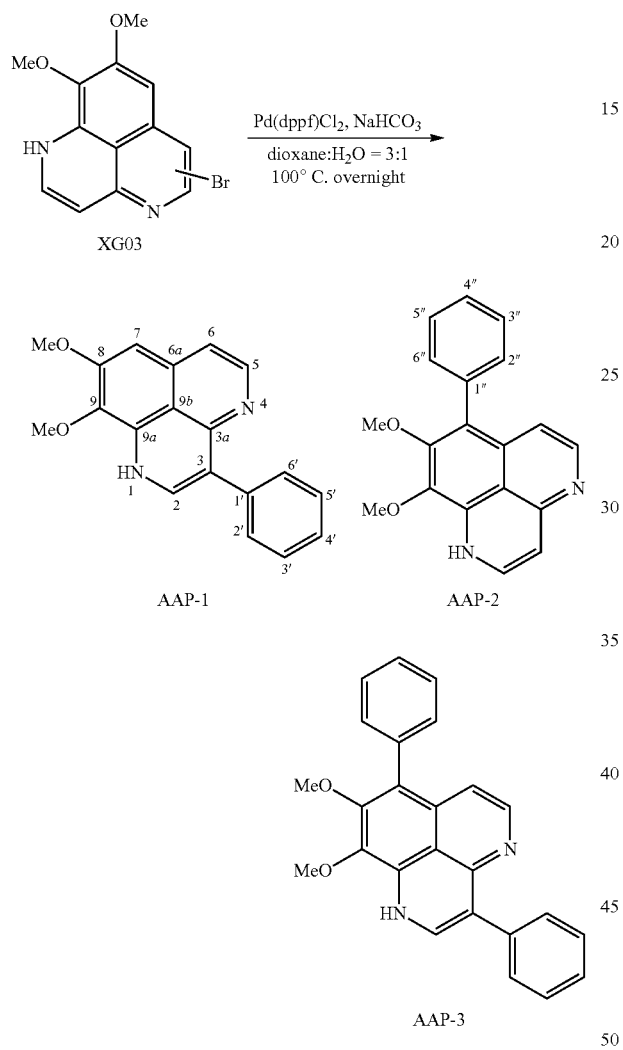

The intermediate XG03 (161 mg, 0.5 mmol), phenylboronic acid (125 mg, 1.03 mmol), Pd(dppf)Cl$_2$ (37 mg, 0.05 mmol) and NaHCO$_3$ (252 mg, 3 mmol) are added to a Dioxane:H$_2$O=3:1 sealed tube, stirred at 100° C. overnight in a nitrogen atmosphere. LC-MS shows two monosubstituted products and one disubstituted product. The reaction mixed solution is added to 5 mL of water and extracted with EtOAc (3×40 mL); an organic phase is dried with anhydrous Na$_2$SO$_4$, and is concentrated to obtain dark green solid; and the solid is subjected to silica gel column chromatography (hexane: acetone=7:3, v/v) to obtain the following:

AAP-1 (1.5 mg), yellow solid, HRESIMS m/z 327.0243 [M+Na]$^+$ (calcd for C$_{19}$H$_{16}$N$_2$O$_2$Na: 327.0241), $^1$H and $^{13}$C NMR (nuclear magnetic resonance) data is shown in Table 1;

AAP-2 (3.1 mg), yellow solid, HRESIMS m/z 327.0243 [M+Na]$^+$ (calcd for C$_{19}$H$_{16}$N$_2$O$_2$Na, 327.0245), $^1$H and $^{13}$C NMR data is shown in Table 2;

AAP-3 (9.0 mg), yellow solid, HRESIMS m/z 403.4056 [M+Na]$^+$ (calcd for C$_{25}$H$_{20}$N$_2$O$_2$Na, 403.4058), $^1$H and $^{13}$C NMR data is shown in Table 3.

4) Synthesis of Hydrochloride of AAP-2

AAP-2 (2 mg, 6.57 mol) is dissolved in 2 mL of ethanol, and an excess of 36.5% hydrochloric acid (10 mL) is slowly added thereto and stirred at room temperature for 30 min, and the solvent is evaporated to dryness at reduced pressure to obtain a hydrochloride of AAP-2.

5) Synthesis of AAP-4, AAP-5 and AAP-6

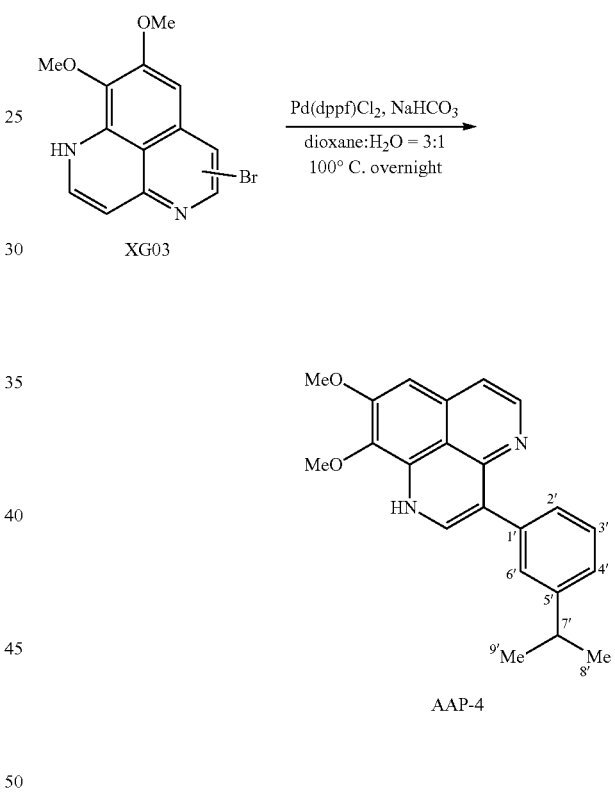

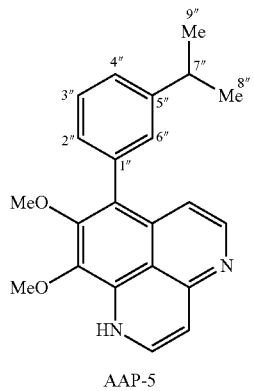

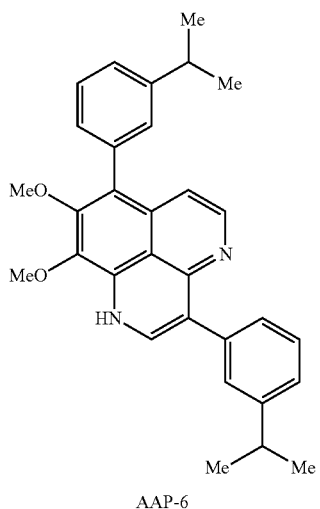

AAP-6

The intermediate XG03 (161 mg, 0.5 mmol), isopropyl-benzeneboronic acid (169 mg, 1.03 mmol), Pd(dppf)Cl$_2$ (37 mg, 0.05 mmol) and NaHCO$_3$ (252 mg, 3 mmol) are added to a Dioxane:H$_2$O=3:1 sealed tube, and stirred at 100° C. overnight in a nitrogen atmosphere; LC-MS shows two monosubstituted products and a disubstituted product; the reaction solution is concentrated and is separated by a thin silica gel plate (DCM:MeOH=30:1, v/v) to obtain the following:

AAP-4 (9.7 mg), yellow solid, HRESIMS m/z 369.1723 [M+Na]$^+$ (calcd for C$_{22}$H$_{22}$N$_2$O$_2$Na, 369.1722), $^1$H and $^{13}$C NMR data is shown in Table 4;

AAP-5 (10.0 mg), yellow solid, HRESIMS m/z 369.1724 [M+Na]$^+$ (calcd for C$_{22}$H$_{22}$N$_2$O$_2$Na, 369.1722), $^1$H and $^{13}$C NMR data is shown in Table 5; and AAP-6 (20.2 mg), yellow solid, HRESIMS m/z 487.2506 [M+Na]$^+$ (calcd for C$_{31}$H$_{32}$N$_2$O$_2$Na, 487.2505), and $^1$H and $^{13}$C NMR data is shown in Table 6.

TABLE 1

$^1$H and $^{13}$C NMR data of compound AAP-1 (C$_{19}$H$_{16}$N$_2$O$_2$)

| position | $\delta_H$, mult, (J in Hz)$^a$ | $\delta_C{}^b$ |
|---|---|---|
| 2 | 7.13, s | 132.8, CH |
| 3 | | 144.5, C |
| 3a | | 134.9, C |
| 5 | 7.70, d, (6.8) | 134.5, CH |
| 6 | 7.11, d, (6.8) | 114.8, CH |
| 6a | | 133.5, C |
| 7 | 6.93, s | 102.6, CH |
| 8 | | 158.8, C |
| 9 | | 134.6, C |
| 9a | | 118.1, C |
| 9b | | 130.5, C |
| 8-OMe | 3.97, s | 57.1, —OCH$_3$ |
| 9-OMe | 4.07, s | 61.3, —OCH$_3$ |
| 1' | | 141.3, C |
| 2', 6' | 7.51, d, (7.2) | 131.0, CH |
| 3', 5' | 7.57, d, (7.2) | 130.2, CH |
| 4' | 7.54, m | 130.4, CH |

$^a$Measured at 400 MHz in CD$_3$OD;
$^b$Measured at 150 MHz in CD$_3$OD.

Table 2 $^1$H and $^{13}$C NMR data of compound AAP-2 (C$_{19}$H$_{16}$N$_2$O$_2$)

| position | $\delta_H$, mult, (J in Hz)$^a$ | $\delta_C{}^b$ |
|---|---|---|
| 2 | 7.13, d | 142.6, CH |
| 3 | 6.44, d | 100.3, CH |
| 3a | | 152.3, C |
| 5 | 7.89, d, (7.2) | 135.1, CH |
| 6 | 6.47, d, (7.2) | 119.9, CH |
| 6a | | 131.4, C |
| 7 | | 129.3, C |
| 8 | | 157.0, C |
| 9 | | 137.9, C |
| 9a | | 112.5, C |
| 9b | | 125.9, C |
| 8-OMe | 4.01, s | 61.6, —OCH$_3$ |
| 9-OMe | 3.73, s | 61.5, —OCH$_3$ |
| 1'' | | 135.9, C |
| 2'', 6'' | 7.53, d, (7.2) | 131.4, CH |
| 3'', 5'' | 7.57, d, (7.2) | 130.0, CH |
| 4'' | 7.54, m | 131.9, CH |

$^a$Measured at 400 MHz in CD$_3$OD;
$^b$Measured at 150 MHz in CD$_3$OD.

TABLE 3

$^1$H and $^{13}$C NMR data of compound AAP-3 (C$_{31}$H$_{32}$N$_2$O$_2$)

| position | $\delta_H$, mult, (J in Hz)$^a$ | $\delta_C{}^b$ |
|---|---|---|
| 2 | 6.98, s | 130.4, CH |
| 3 | | 129.8, C |
| 3a | | 150.2, C |
| 5 | 8.20, d, (7.6) | 133.8, CH |
| 6 | 7.23, d, (7.6) | 119.7, CH |
| 6a | | 127.0, C |
| 7 | | 123.3, C |
| 8 | | 158.6, C |
| 9 | | 136.0, C |
| 9a | | 113.2, C |
| 9b | | 124.7, C |
| 8-OMe | 4.04, s | 57.0, —OCH$_3$ |
| 9-OMe | 3.76, s | 60.6, —OCH$_3$ |
| 1' | | 142.0, C |
| 2', 6' | 7.34, m | 128.3, CH |
| 3', 5' | 7.37, m | 129.1, CH |
| 4' | 7.33, m | 128.0, CH |
| 1'' | | 136.5, C |
| 2'', 6'' | 7.51, d, (7.2) | 127.9, CH |
| 3'', 5'' | 7.46, m | 129.2, CH |
| 4'' | 7.41, m | 127.6, CH$_3$ |

$^a$Measured at 400 MHz in CD$_3$OD;
$^b$Measured at 150 MHz in CD$_3$OD.

TABLE 4

$^1$H and $^{13}$C NMR data of compound AAP-4 (C$_{22}$H$_{22}$N$_2$O$_2$)

| position | $\delta_H$, mult, (J in Hz)$^a$ | $\delta_C{}^b$ |
|---|---|---|
| 2 | 6.72, s | 127.7, CH |
| 3 | | 126.1, C |
| 3a | | 149.8, C |
| 5 | 8.00, d, (7.6) | 132.1, CH |
| 6 | 7.31, d, (7.6) | 113.0, CH |
| 6a | | 134.0, C |
| 7 | 6.90, s | 101.4, CH |
| 8 | | 157.1, C |
| 9 | | 136.0, C |
| 9a | | 116.8, C |
| 9b | | 121.5, C |
| 8-OMe | 4.03, s | 56.6, —OCH$_3$ |
| 9-OMe | 3.99, s | 61.6, —OCH$_3$ |
| 1' | | 139.2, C |
| 2' | 7.19, s | 129.6, CH |
| 3' | 7.19, s | 130.2, CH |

TABLE 4-continued $^{1}$H and $^{13}$C NMR data of compound AAP-4 (C$_{22}$H$_{22}$N$_{2}$O$_{2}$)

| position | $\delta_H$, mult, (J in Hz)$^a$ | $\delta_C^b$ |
|---|---|---|
| 4' | 7.19, s | 128.6, CH |
| 5' |  | 148.1, C |
| 6' | 7.26, s | 127.3, CH |
| 7' | 2.89, m | 34.3, CH |
| 8' | 1.22, d (6.8) | 24.2, CH$_3$ |
| 9' | 1.22, d (6.8) | 24.1, CH$_3$ |

$^a$Measured at 400 MHz in CD$_3$OD;
$^b$Measured at 150 MHz in CD$_3$OD.

TABLE 5

$^{1}$H and $^{13}$C NMR data of compound AAP-5 (C$_{22}$H$_{22}$N$_{2}$O$_{2}$)

| position | $\delta_H$, mult, (J in Hz)$^a$ | $\delta_C^b$ |
|---|---|---|
| 2 | 6.94, d | 140.5, CH |
| 3 | 6.43, d | 99.5, CH |
| 3a |  | 150.7, C |
| 5 | 7.94, d, (5.2) | 133.4, CH |
| 6 | 7.13, d, (5.2) | 118.6, CH |
| 6a |  | 127.3, C |
| 7 |  | 124.5, C |
| 8 |  | 155.4, C |
| 9 |  | 134.1, C |
| 9a |  | 111.3, C |
| 9b |  | 126.1, C |
| 8-OMe | 4.06, s | 61.2, —OCH$_3$ |
| 9-OMe | 3.74, s | 61.0, —OCH$_3$ |
| 1" |  | 136.5, C |
| 2" | 7.10, m | 128.5, CH |
| 3" | 7.25, m | 130.4, CH |
| 4" | 7.10, m | 128.1, CH |
| 5" |  | 149.5, C |
| 6" | 7.41, s | 128.7, CH |
| 7" | 3.00, m | 33.9, CH |
| 8", 9" | 1.27, d, (6.8) | 23.9, CH$_3$ |

$^a$Measured at 400 MHz in CD$_3$OD; $^b$ Measured at 150 MHz in CD$_3$OD.

TABLE 6

$^{1}$H and $^{13}$C NMR data of compound AAP-6 (C$_{31}$H$_{32}$N$_{2}$O$_{2}$)

| position | $\delta_H$, mult, (J in Hz)$^a$ | $\delta_C^b$ |
|---|---|---|
| 2 | 6.37, S | 26.0, CH |
| 3 |  | 113.5, C |
| 3a |  | 150.6, C |
| 5 | 8.07, d, (5.2) | 133.7, CH |
| 6 | 7.20, d, (5.2) | 118.4, CH |
| 6a |  | 127.1, C |
| 7 |  | 124.3, C |
| 8 |  | 155.0, C |
| 9 |  | 134.4, C |
| 9a |  | 110.9, C |
| 9b |  | 126.1, C |
| 8-OMe | 4.03, s | 61.3, —OCH$_3$ |
| 9-OMe | 3.74, s | 61.0, —OCH$_3$ |
| 1' |  | 141.9, C |
| 2' | 7.41, m | 129.3, CH |
| 3' | 7.46, m | 131.2, CH |
| 4' | 7.39, m | 127.2, CH |
| 5' |  | 149.4, C |
| 6' | 7.53, m | 129.8, CH |
| 7' | 2.89, m | 33.9, CH |
| 8', 9' | 1.21, d, (6.8) | 23.8, CH$_3$ |
| 1" |  | 136.9, C |
| 2" | 7.29, m | 128.1, CH |
| 3" | 7.20, m | 130.3, CH |
| 4" | 7.12 | 127.3, CH |
| 5" |  | 148.2, C |
| 6" | 7.37, m | 128.7, CH |
| 7" | 2.96, m | 34.0, CH |
| 8", 9" | 1.29, d | 24.0, CH$_3$ |

$^a$Measured at 400 MHz in CD$_3$OD;
$^b$Measured at 150 MHz in CD$_3$OD.

Embodiment 2 In Vitro Antitumor Activity Test of the Compounds of the Present Invention In vitro anti-lung cancer stem cell test is carried out on the compounds AAP-1-6 of the present invention, and the lung cancer stem cell lines used are as follows:

Human lung cancer cell PC9 is purchased from ATCC with ATCC number 32727.

The human lung cancer cell PC9 is cultured in vitro to form a sphere so that the lung cancer stem cells are maintained in an undifferentiated state for 3 months, and the results of Western blot and flow analysis show that the lung cancer stem cells which are enriched through in vitro sphere formation highly express ALDH1 and CD44. In addition, Oct4-GFP and Nanog-GFP are highly expressed by lentivirus transfection. Western blot shows that the expression levels of CD44 and ALDH1 are improved correspondingly after the high expression of Oct4 and Nanog. The immunofluorescence results also shows that CD44 and ALDH1 are localized to cells with Oct4+ and Nanog+, which indicates that such cells have lung cancer stem cell characteristics.

The original cell culture medium for Human lung cancer stem cells PC9-Nanog and PC9-Oct4 is discarded, 3 mL of PBS is added to rinse the cells twice; 500 µL of 0.25% trypsin is then added for digestion for 3 minutes at 37° C.; and 3 mL of a complete medium is added to terminate the digestion. The cells are pipetted gently with a pipette to make a single cell suspension; the single cell suspension is transferred to a 15 mL centrifuge tube and centrifuged at 800 rpm for 4 minutes; the supernatant is discarded, 6 mL of a complete medium is added to the centrifuge tube, and mixed by pipetting; counting is carried out to prepare 3×10$^5$ cells/ml single cell suspension; the suspension is added to a 96-well plate, 90 µL per well, (wells at the outer ring are not added with the suspension), and finally each well has 3000 cells; and the 96-well plate is incubated for 24 hours in a 37° C., 5% CO$_2$ incubator.

1 mg of each of the compounds AAP-1, AAP-2, AAP-3, AAP-4, AAP-5, and AAP-6 of the present invention is prepared into a 10 mM stock solution by using DMSO, and stored in a refrigerator with a temperature of 4° C. Thereafter, the stock solution is diluted with a medium to a 10 µM test solution. The final concentration is 10 µM in a 96-well plate, and the test solution is diluted three folds and added to the plate. Finally, the concentrations of the test solutions of the compounds of the present invention added to the plate are 10 µM, 3.3 µM, 1.1 µM, and 0.33 µM, respectively. The 96-well plate added with the compounds is incubated for 72 hours in a 37° C., 5% CO$_2$ incubator. 72 hours later, 10 µL of CCK-8 solution is added to each well. 40 minutes to 60 minutes later, the absorbance at 450 nM, i.e., the OD value, is measured with a microplate reader. Cell viability is calculated after measuring the OD value of each group of cells.

Cell viability (%)=(OD value of the treated group−OD value of the blank group)/(OD value of the blank control group−OD value of the blank group)×100%

The blank control group is not added with the compounds of the present invention, and the other steps are the same.

Meanwhile, the positive control drugs Cis-platinum (Shanghai Boliang Biotechnology Co., Ltd.) and Aaptamine (Reference: Enrique L. Larghi, Maria L. Bohn, Teodoro S. Kaufman, Aaptamine and related products. Their isolation, chemical syntheses, and biological activity, *Tetrahedron* 2009, 65 (22), 4257-4282 synthesis) are used as control groups for in vitro anti-tumor activity test, and the treatment method herein is the same as that for the compounds of the present invention.

The activity data of the compounds is shown in Table 7:

TABLE 7

Half effective inhibitory concentrations (μM) of compounds AAP-1 to AAP-6 and control compounds against tumor cells
$IC_{50}$ (μM)

| | AAP-1 | AAP-2 | AAP-3 | AAP-4 | AAP-5 | AAP-6 | Cis-platinum | Aaptamine |
|---|---|---|---|---|---|---|---|---|
| PC9-Oct4 | 1.04 ± 0.11 | 7.22 ± 0.04 | 5.18 ± 0.11 | 5.66 ± 0.04 | 3.59 ± 0.07 | 3.82 ± 0.15 | 3.24 ± 0.05 | 8.44 ± 0.10 |
| PC9-Nanog | 1.24 ± 0.02 | 6.82 ± 0.16 | 9.77 ± 0.22 | 2.14 ± 0.09 | 3.33 ± 0.03 | 4.82 ± 0.12 | 4.53 ± 0.03 | 10.11 ± 0.17 |

As can be seen from Table 7, the compounds AAP-1 to AAP-6 of the present invention show good inhibitory effects on two lung cancer stem cells, and their $IC_{50}$ values at 1.04-9.77 μM are superior to those of the positive control drugs cisplatin and Aaptamine.

The present invention provides new lead compounds for the research and development of new anti-lung cancer drugs.

Embodiment 3 In Vitro Antifungal Activity Test of the Compounds of the Present Invention A microdilution method (Pierce C G, Uppuluri P, Tristan A R, et al. A simple and reproducible 96-well plate-based method for the formation of fungal biofilms and its application to antifungal susceptibility testing [J]. Nat Protoc, 2008, 3 (9): 1494-1500.) is adopted, and its experimental procedure refers to the M38-A2 and M27-A2 solutions (Espinel-Ingroff A, Fothergill A, Fuller J, et al. Wild-type MIC distributions and epidemiological cutoff values for caspofungin and *Aspergillus* Spp. for the CLSI broth microdilution method (M38-A2 document) [J]. Antimicrobl Agents Chemother, 2011, 55 (6): 2855-2859.). Three tested strains (*Candida albicans, Trichophyton mentaqrophytes* and *Trichophyton rubrum*) are used as indicator bacteria to carry out in vitro antifungal drug sensitivity screening experiment for the compounds AAP-1-AAP6.

Control drugs: ketoconazole (purchased from Shanghai Boliang Biotechnology Co., Ltd.), Aaptamine (same as Embodiment 2).

The activity data of the compounds is shown in Table 8:

TABLE 8

Antifungal activity of compounds AAP-1 to AAP-6 and control compounds
MIC (μg/mL)

| | AAP-1 | AAP-2 | AAP-3 | AAP-4 | AAP-5 | AAP-6 | Ketoconazole | Aaptamine |
|---|---|---|---|---|---|---|---|---|
| *Candida albicans* | >30 | >30 | 12.5 | >30 | 12.5 | 25 | 8 | >30 |
| *Trichophyton mentaqrophytes* | 25 | 25 | >30 | >30 | 12.5 | >30 | 8 | >30 |
| *Trichophyton rubrum* | 12.5 | 25 | >30 | >30 | 3.125 | >30 | 8 | >30 |

The activity results show that the MIC of AAP-5 against *Trichophyton rubrum* is 3.125 μg/mL, which is better than that of the positive control drugs ketoconazole (MIC=8 μg/mL) and Aaptamine (MIC>30 μg/mL).

The preferred embodiments of the present invention have been specifically described above, but the present invention is not limited to these embodiments, and those skilled in the art can make various equivalents without departing from the inventive spirit of the present invention. These equivalent variations or substitutions are intended to be included within the scope as defined by the appended Claims of the present application.

What is claimed is:

1. A benzodiazepine alkaloid compound and pharmaceutically acceptable salts thereof, wherein the structure of the compound is as shown in a general formula (I):

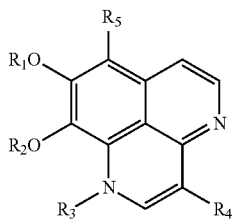

(I)

in the formula (I), $R_1$, $R_2$ and $R_3$ are independently H, $C_{1-4}$ alkyl or $C_{1-4}$ alkanoyl;

one of $R_4$ and $R_5$ is a benzene ring or a substituted benzene ring, the other is H, a benzene ring or a substituted benzene ring, and a substituent on the substituted benzene ring is hydroxyl, cyano, amino, halogen, $C_{1-4}$ alkyl, $C_{1-4}$ alkoxy, $C_{1-4}$ alkylamine, $C_{1-4}$ alkanoyl or $C_{1-4}$ alkoxyacyl.

2. The benzodiazepine alkaloid compound according to claim 1, wherein $R_1$ and $R_2$ are methyl and $R_3$ is H.

3. The benzodiazepine alkaloid compound according to claim 2, wherein the substituted benzene ring is a mono-substituted or disubstituted benzene ring.

4. The benzodiazepine alkaloid compound according to claim 2, wherein the halogen is Fl, Cl or Br; the $C_{1-4}$ alkyl is methyl or isopropyl; and the $C_{1-4}$ alkoxy is methoxy.

5. The benzodiazepine alkaloid compound according to claim 1, wherein the compound is

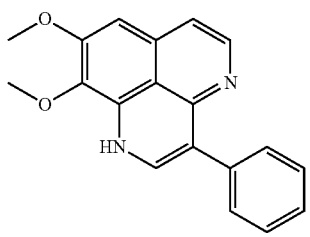

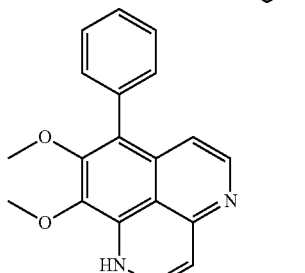

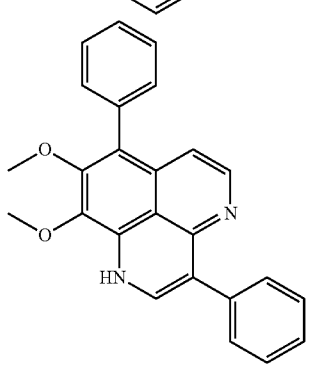

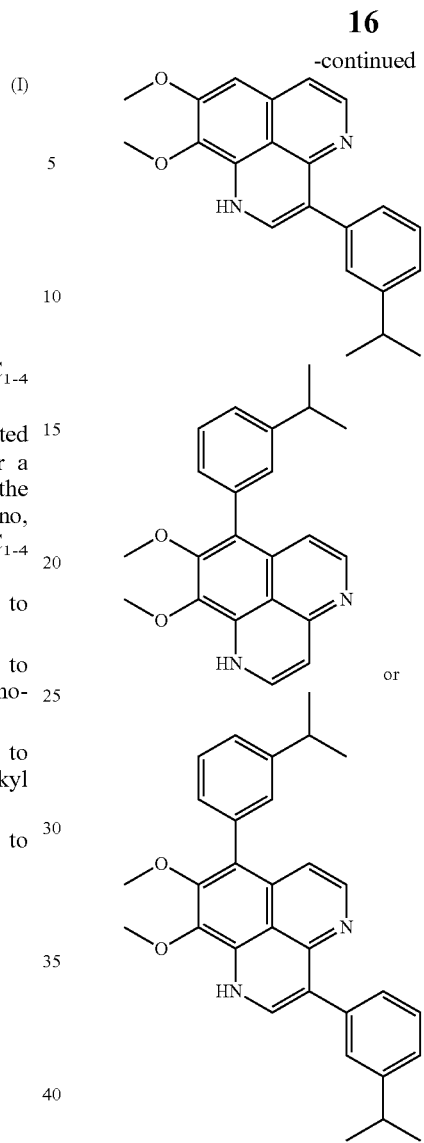

or

6. The benzodiazepine alkaloid compound according to claim 1, wherein the pharmaceutically acceptable salts are salts of an organic acid, salts of an inorganic acid or salts of an alkali.

7. The benzodiazepine alkaloid compound according to claim 6, wherein the inorganic acid is hydrochloric acid, sulfuric acid, phosphoric acid, diphosphoric acid, hydrobromic acid or nitric acid.

8. The benzodiazepine alkaloid compound according to claim 6, wherein the organic acid is acetic acid, maleic acid, fumaric acid, tartaric acid, succinic acid, lactic acid, p-toluenesulfonic acid, salicylic acid or oxalic acid.

9. The benzodiazepine alkaloid compound according to claim 6, wherein the alkali is lithium hydroxide, sodium hydroxide, calcium hydroxide, potassium hydroxide, aqueous ammonia, sodium carbonate or sodium hydrogencarbonate.

10. A method for synthesizing the benzodiazepine alkaloid compound according claim 1, comprising the steps of:
    (a) carrying out a bromine substitution reaction between an intermediate A and $Br_2$ to obtain a monobromo or dibromo intermediate B; and
    (b) reacting the intermediate B with phenylboronic acid or substituted phenylboronic acid to obtain a compound of formula (I);

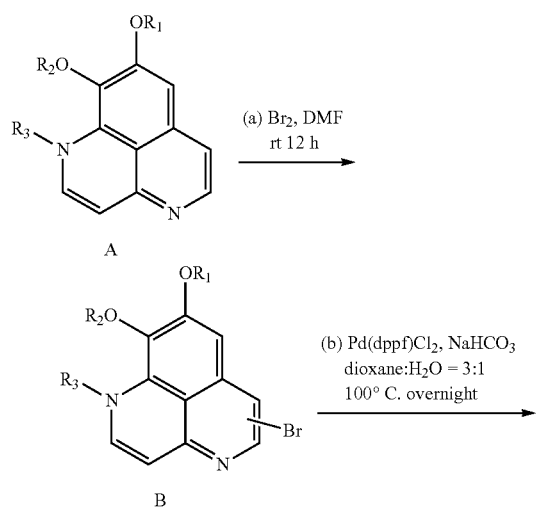

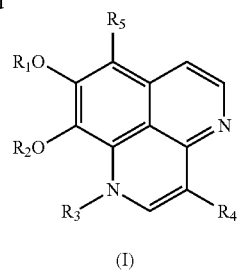

(I)

wherein $R_1$, $R_2$ and $R_3$ are independently H, $C_{1-4}$ alkyl or $C_{1-4}$ alkanoyl-; one of $R_4$ and $R_5$ is a benzene ring or a substituted benzene ring, the other is H, a benzene ring or a substituted benzene ring, and a substituent on the substituted benzene ring of phenylboronic acid is hydroxyl, cyano, amino, halogen, $C_{1-4}$ alkyl, $C_{1-4}$ alkoxy, $C_{1-4}$ alkylamine, $C_{1-4}$ alkanoyl or $C_{1-4}$ alkoxyacyl.

* * * * *